United States Patent [19]

Sprague et al.

[11] Patent Number: 4,500,723
[45] Date of Patent: Feb. 19, 1985

[54] 7-OXABICYCLOHEPTAINE PROSTAGLANDIN INTERMEDIATES AND METHOD FOR PREPARING SAME

[75] Inventors: Peter W. Sprague, Pennington; James E. Heikes, East Windsor, both of N.J.

[73] Assignee: E. R. Squibb & Sons, Inc., Princeton, N.J.

[21] Appl. No.: 494,235

[22] Filed: May 13, 1983

[51] Int. Cl.³ .................................. C07D 307/88
[52] U.S. Cl. .................................. 549/459
[58] Field of Search ........................ 549/459

[56] References Cited

U.S. PATENT DOCUMENTS 4,143,054  3/1979  Sprague .......................... 549/459

OTHER PUBLICATIONS

Orchin et al., The Vocabulary of Organic Chem., John Wiley Publishers, pp. 122, 130, 131 and 144, (1980).
Haslanger et al., Synthesis, Oct. 1981, pp. 801–802.
Woodward et al., J.A.C.S., vol. 95 (20), pp. 6853–6855, (1973).
Mitra, The Synthesis of Prostaglandins, Wiley, p. 12, (1977).
Sprague et al., Advances in Prostaglandins and Thromboxane Research, vol. 6, pp. 493–496, (1980).

*Primary Examiner*—Henry R. Jiles
*Assistant Examiner*—Bernard I. Dentz
*Attorney, Agent, or Firm*—Lawrence S. Levinson; Burton Rodney

[57] ABSTRACT

7-Oxabicycloheptane prostaglandin intermediates are provided having the general structure

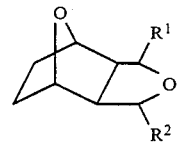

wherein one of $R^1$ and $R^2$ is

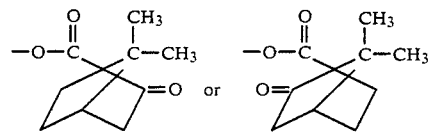

and the other is hydrogen.

A method for preparing the above intermediates is also provided.

8 Claims, No Drawings

7-OXABICYCLOHEPTAINE PROSTAGLANDIN INTERMEDIATES AND METHOD FOR PREPARING SAME

FIELD OF THE INVENTION

The present invention relates to optically active intermediates for use in preparing 7-oxabicycloheptane prostaglandin analogs and to a method for preparing such intermediates.

BACKGROUND OF THE INVENTION

U.S. Pat. No. 4,413,054 to Sprague dated Mar. 6, 1979 discloses 7-oxabicycloheptane and 7-oxabicycloheptene prostaglandin analogs which are prepared by the following methods.

In a first method maleic anhydride is made to react with an unsubstituted or substituted furan of the formula

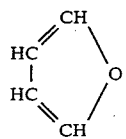

to form a compound of the formula

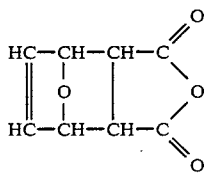

which is reduced to form

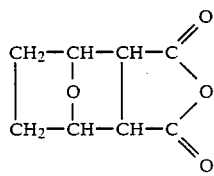

The above compound is then further reduced to form

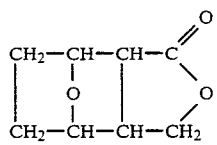

A

Treatment of the above compound with diisobutylaluminum hydride or diisobutylborane yields

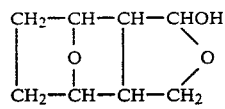

B

Submitting compound A to Wittig reaction conditions produces

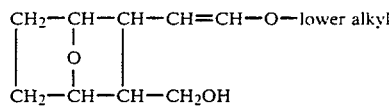

C

Compound C is then acylated and then hydrolyzed to form the aldehyde

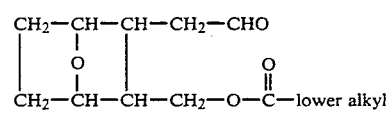

D

All of the above compounds are in the form of racemic mixtures.

Aldehyde D is subjected to a Wittig reaction to form a compound of the structure

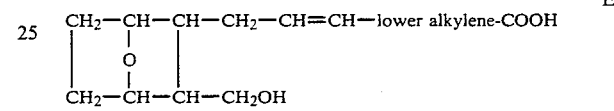

E which is esterified to form the corresponding lower alkyl ester. The hydroxymethyl group in the 3-position of the ester is then oxidized to obtain the aldehyde

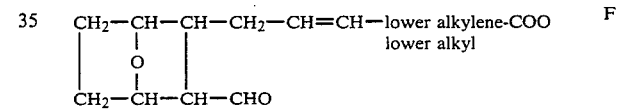

F

Aldehyde F which is in the form of a racemic mixture is employed to form 7-oxabicycloheptane prostaglandin analogs.

BRIEF DESCRIPTION OF THE INVENTION

In accordance with the present invention, a method is provided for forming the aldehyde D also depicted graphically as

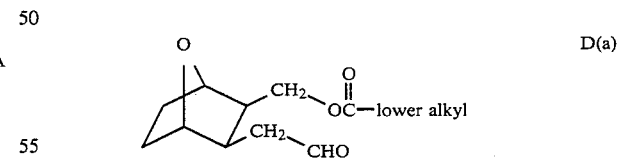

D(a)

in the form of its optically active isomer as opposed to a racemic mixture of two enantiomers as disclosed by Sprague in U.S. Pat. No. 4,143,054. The optically active aldehyde D(a) is then employed to form optically active 7-oxabicycloheptane prostaglandin analogs, for example, using the technique described by Sprague in U.S. Pat. No. 4,143,054.

In carrying out the method of the invention as described hereinafter several novel optically active intermediates are formed having the following formula

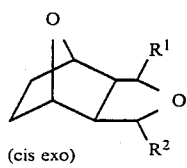

wherein one of R¹ and R² is

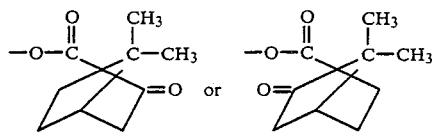

and the other is H, and includes the following compounds:

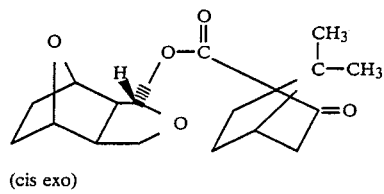

II

[1S-[1α(1S),3aα,4α,7α,7aα]]-Octahydro-1-[[2-oxo-7,7-dimethylbicyclo[2.2.1]heptane]carboxyl]-4,7-epoxyisobenzofuran

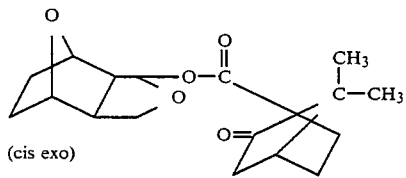

III

[1S-[1α(1R),3aα,4α,7α,7aα]]-Octahydro-1-[[2-oxo-7,7-dimethylbicyclo[2.2.1]heptane]carboxyl]-4,7-epoxyisobenzofuran

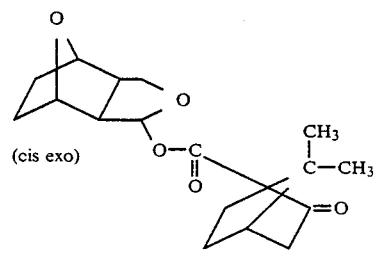

IV

[1R-[1α(1S),3aα,4α,7α,7aα]]-Octahydro-1-[[2-oxo-7,7-dimethylbicyclo[2.2.1]heptane]carboxyl]-4,7-epoxyisobenzofuran

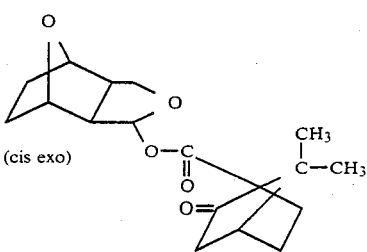

V

[1R-[1α(1R),3aα,4α,7α,7aα]]-Octahydro-1-[[2-oxo-7,7-dimethylbicyclo[2.2.1]heptane]carboxyl]-4,7-epoxyisobenzofuran The method of the present invention for forming optically active or chiral intermediates for use in preparing optically active 7-oxabicycloheptane prostaglandin analogs may be summarized in the following reaction sequence.

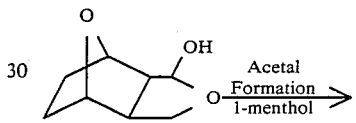

G
cis exo or cis endo

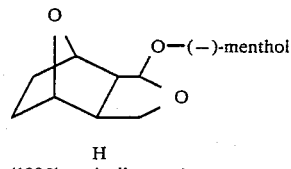

H
(100% optically pure)

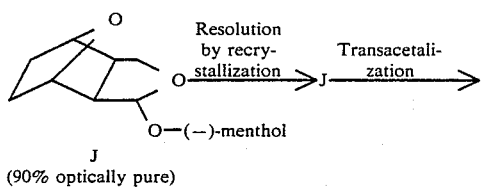

J
(90% optically pure)

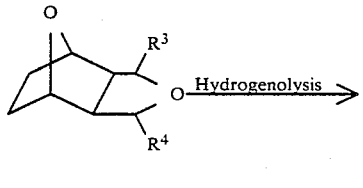

K
(R⁴ is —O—CH₂—⌬
and R³ is H)
(optically active)

-continued

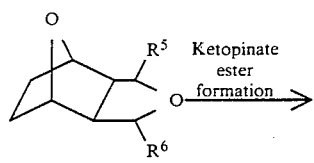

L
($R^6$ is OH and $R^5$ is H)
(90% optically pure)

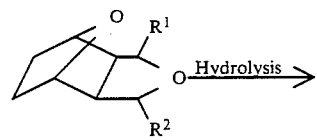

II (III)
(wherein $R^2$ is

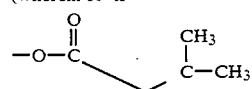

=O or

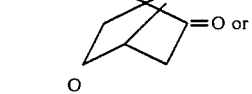

and $R^1$ is H)
(optically active)

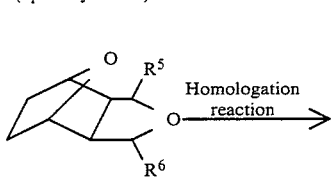

M
(100% optically active)
($R^6$ is OH and $R^5$ is H)

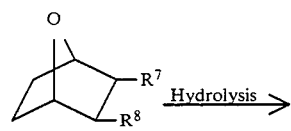

N
($R^7$ is $CH_2OH$ and $R^8$ is $-CH=CH-OCH_3$)
(optically active)

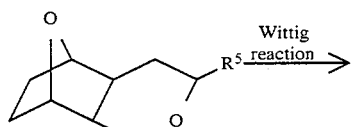

(wherein $R^6$ is H and $R^5$ is OH) (optically active)

-continued

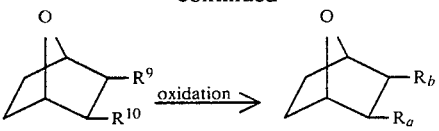

P
($R^9$ is $-CH_2-CH=CH-$lower alkylene-$CO_2CH_3$ and $R^{10}$ is $-CH_2OH$) (optically active)

Q
(one of $R_a$ is $-CH_2-CH=CH-$lower alkylene-$CO_2CH_3$ and $R_b$ is $-CHO$) (optically active)

DETAILED DESCRIPTION OF THE INVENTION

The method of the invention is an advance over prior art methods for forming optically active 7-oxabicycloheptane prostaglandin analogs in that the resolution is performed at a very early stage of the synthesis, preferably on a hemi-acetal intermediate. In the present method, the undesired menthol diastereomer can be separated out and recycled. Thus, in principle, the hemi-acetal intermediate is transformed to a single diastereomer.

In carrying out the method of the invention, referring to the above reaction sequence, the racemic cis-exo hemiacetal

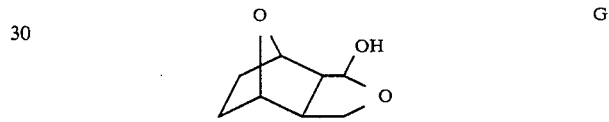

is converted to a diastereomeric mixture of menthol compounds H and J by reacting same with 1-menthol in the presence of trace amounts of p-toluenesulfonic acid and an inert solvent such as benzene at reflux temperatures under an inert atmosphere, for example, nitrogen to form a mixture of diastereomers of formula H and J which is recrystallized, for example, from methanol and resolved to form the optically active acetal isomer J

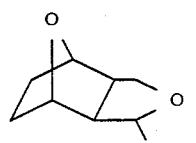

O—(—)-menthol
(90% optically pure)

The acetal J is allowed to react with benzyl alcohol at elevated temperatures of at least 110° to form the optically active benzyloxy compound

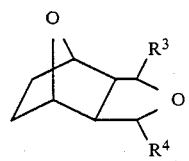

(wherein $R^4$ is benzyloxy and $R^3$ is H) which is subjected to a hydrogenolysis reaction, for example, by reaction with hydrogen in the presence of palladium on charcoal to form the optically active hemiacetal

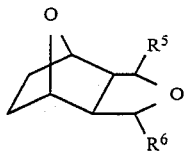

L (wherein R⁶ is OH and R⁵ is H, 90% optically active).

The hemiacetal L (90% optically pure) is reacted with l-ketopinic acid halide, such as the chloride (prepared as described in U.S. Pat. No. 4,235,891) employing a molar ratio of L:ketopinic acid chloride of about 0.5:1 to about 1:1, in the presence of 4-dimethylaminopyridine or (4-diethylaminopyridine and dicyclohexylcarbodiimide) and an inert solvent such as pyridine or dichloromethane to form a ketopinate ester II or III (where l-ketopinic acid halide is used).

The reaction sequence for preparing the optically active antipodes of compounds of formulae II and III, namely compounds of formulae IV and V, respectively, may be prepared following the above reaction sequence except that d-ketopinic acid halide is employed in place of the corresponding l-isomer.

The optically active ketopinate II (III) may then be subjected to ester hydrolysis, for example, by reacting the ketopinate with lithium hydroxide and hydrogen peroxide to form the optically active hemiacetal M

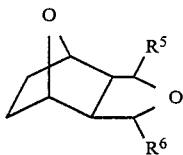

M (wherein R⁶ is OH and R⁵ is H) (100% optically active).

The hemiacetal M may then be employed to form optically active hemiacetal O by subjecting hemiacetal M to a homologation reaction, for example, by submitting M to Wittig reaction conditions by reacting M with an (alkoxymethyl)triphenylphosphonium halide such as (methoxymethyl)triphenylphosphonium chloride in the presence of an alkylamine like diisopropylamine, a lithium alkyl like n-butyl lithium in an inert organic medium like hexane, tetrahydrofuran or the like, at a temperature in the range of about −10° to 25° C. to form optically active compound N

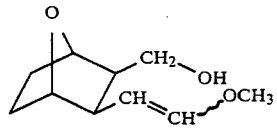

N (wherein R⁷ is CH₂OH and R⁸ is —CH=CH—OCH₃).

Hydrolysis of alcohol compound N in the presence of strong acid such as trifluoroacetic acid produces optically active hemiacetal O which is then subjected to Wittig reaction conditions and esterification, for example, reaction with a carboxyalkyl triphenylphosphonium halide, such as, triphenylcarboxybutylphosphonium chloride, in the presence of inert solvent, such as DMSO, to form optically active alcohol which is then reacted with, for example, a diazoalkane like diazomethane, to form the alcohol ester P

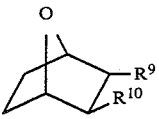

P (wherein R¹⁰ is —CH₂—CH=CH-lower alkylene CO₂CH₃ and R⁹ is —CH₂OH)

The optically active alcohol ester M may then be oxidized, for example, by reaction with chromium oxide with pyridine to form the optically active aldehyde O.

Thus, it is seen that the aldehyde O may be prepared from the starting hemiacetal without recourse to any chromatographic purification.

The prostaglandin aldehyde analog O may then be employed to prepare 7-oxabicycloheptane prostaglandins following the procedure as set out in U.S. Pat. No. 4,143,054 to Sprague. Such prostaglandin derivatives are useful in the treatment of thrombolytic disease as explained in the above Sprague patent.

The nucleus in each of the compounds of the invention is depicted as

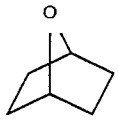

for matter of convenience; it will also be appreciated that the nucleus in the compounds of the invention may be depicted as

O.

The following Examples represent preferred embodiments of the present invention. All temperatures are expressed in degrees Centigrade.

EXAMPLE 1

[1R-[1α(1S),3aα,4α,7α,7aα]]-Octahydro-1-[[2-oxo-7,7-dimethylbicyclo[2.2.1]heptane]carboxyl]-4,7-epoxyisobenzofuran

A.
[1S-[1α(1R,2S,5R),3aα,4α,7α,7aα]]-Octahydro-1-[[5-methyl-2-(1-methylethyl)-cyclohexyl]oxy]-4,7-epoxyisobenzofuran and

B.
[1R-[1α(1R,2S,5R),3aα,4α,7α,7aα]]-Octahydro-1-[[5-methyl-2-(1-methylethyl)-cyclohexyl]oxy]-4,7-epoxyisobenzofuran A solution of (exo)-octahydro-4,7-epoxyisobenzofuran-1-ol (prepared as described in U.S. Pat. No. 4,143,054) (30 g, 0.192 mole), levo-menthol (30 g, 0.192 mole) and p-toluenesulfonic acid (100 mg) in benzene (500 ml) was heated at reflux for 24 hours under nitrogen with a Dean-Stark trap containing molecular sieves in the system. The solution was chilled, washed with 5% sodium bicarbonate (100 ml), then concentrated in vacuo. The residue was recrystallized from methanol (300 ml) to yield 15 g of pure isomer A, m.p. 109°–111°

C. The mother liquor was concentrated in vacuo. The residue was chromatographed on LP-1 silica gel (600 ml) eluting with hexane and ether/hexane (1:9) to yield 20 g of isomeric mixture A and B. This mixture was recrystallized from methanol (150 ml) to yield 7 g of pure isomer A (100% optically pure), m.p. 109°–111° C. The mother liquor was concentrated to yield 24 g of isomer B which was approximately 90% optically pure by C-13 NMR.

C.
[1S,3aR-(1α,3aα,4α,7α,7aα)]-Octahydro-1-benzyloxy-4,7-epoxyisobenzofuran

A solution of isomer B (prepared as described above) (24 g. 0.082 mole) and p-toluenesulfonic acid (100 mg) in benzyl alcohol (250 ml) was heated at 90° C. for 90 minutes. TLC (silica gel; ether/hexane (1:1)) indicated complete absence of starting material. The mixture was chilled, diluted with ether (1000 ml), washed with 5% sodium bicarbonate, then concentrated in vacuo. Excess benzyl alcohol was removed by distillation. The residue was dissolved in hexane (200 ml) and chilled overnight to yield 13 g of title C compound, an oil at room temperature.

TLC: silica gel; hexane/ether (1:1), $R_f$=0.2; vanillin spray and heat.

D.
[3aR-(3aα,4α,7α,7aα)]-Octahydro-4,7-epoxyisobenzofuran-1-ol

A solution of title C compound (13 g, 0.053 mole) and trifluoroacetic acid (40 ml) in water (160 ml) was stirred at room temperature under nitrogen for 4 hours. The mixture was neutralized with solid sodium bicarbonate, saturated with sodium chloride and extracted with dichloromethane (8×200 ml). The combined extracts were dried over magnesium sulfate and concentrated in vacuo. The residue was chromatographed on LP-1 silica gel (500 ml) eluting with ethyl acetate/dichloromethane (2:5) to yield 8 g of title D compound (90% optically pure).

TLC: silica gel; ethyl acetate/dichloromethane (1:1); $R_f$=0.2; vanillin spray and heat.

E.
[1R-[1α(1S),3aα,4α,7α,7aα]]-Octahydro-1-[[2-oxo-7,7-dimethylbicyclo[2.2.1]heptane]carboxyl]-4,7-epoxyisobenzofuran A solution of title D compound (8.75 g, 0.056 mole), levo-ketopinic acid (Org. Syn., 45, p. 55) (10.21 g, 0.056 mole), 4-dimethylaminopyridine (6.84 g, 0.056 mole) and dicyclohexylcarbodiimide (11.55 g, 0.056 mole) in dichloromethane (200 ml) was stirred at room temperature under nitrogen for 4 days. The mixture was filtered and the filtrate washed with 5% potassium bisulfate (2×100 ml), 5% sodium bicarbonate (2×100 ml) and water. The organic layer was dried over magnesium sulfate and concentrated in vacuo. The residue was recrystallized 3 times from diisopropyl ether to yield 10 g of title compound, m.p. 148°–150° C.

TLC: silica gel; ether/hexane (1:1), $R_f$=0.2; vanillin spray and heat.

$[\alpha]_D$= +48° C=20 mg/ml (CHCl$_3$)

EXAMPLE 2
[1S-(1α,2β(Z),3β,4α)]-7-[3-(Hydroxymethyl)-7-oxabicyclo[2.2.1]hept-2-yl]-5-heptenoic acid, methylester

A.
[3aR-(1α,3aα,4α,7α,7aα)]-Octahydro-4,7-epoxyisobenzofuran-1-ol

A solution of Example 1 compound (8.8 g, 0.0275 mole) in tetrahydrofuran (150 ml) was treated with 1N sodium hydroxide (55 ml. 0.055 mole) and stirred at room temperature for 4 hours. The reaction mixture was treated with 1N hydrochloric acid (55 ml, 0.055 mole), saturated with sodium chloride, and extracted with chloroform (10×100 ml). The combined extracts were dried over magnesium sulfate and concentrated in vacuo. The residue was chromatographed on LP-1 silica gel (500 ml) eluting with dichloromethane and ethyl acetate/dichloromethane (1:1) to yield 4 g of product which was recrystallized from benzene/cyclohexane to yield 3.7 g of title A compound, m.p. 65°–67° C.

TLC: silica gel; ethyl acetate/dichloromethane (1:1); $R_f$=0.2; vanillin spray and heat. $[\alpha]_D$= +46° C=20 mg/ml (CHCl$_3$).

B.
[(1R-(1α,2β,3β,4α)]-3-(2-Methoxyethenyl)-7-oxabicyclo[2.2.1]heptane-2-methanol A slurry of methoxymethyltriphenylphosphonium chloride (15.2 g, 0.0443 mole) in toluene (500 ml) was treated with a solution of lithium diisopropylamide (prepared from 1.6M n-butyl lithium (27.6 ml, 0.0442 mole) and diisopropylamine (7.7 ml, 0.055 mole) in pentane in tetrahydrofuran (10 ml) at 0° C. The mixture was stirred at room temperature for 30 minutes then treated via a solid addition device with title A compound (2 g, 0.0128 mole). The mixture was stirred at room temperature for 3 days then poured into brine (1000 ml), treated with 10% hydrochloric acid until pH=6.5, then extracted with ether (3×200 ml). The combined ether extracts were dried over magnesium sulfate and concentrated in vacuo. The residue was triturated with hexane/ether and filtered. The filtrate was concentrated in vacuo. The residue was chromatographed on LP-1 silica gel (300 ml) eluting with dichloromethane and ether/dichloromethane (1:1) to yield the desired product contaminated with phosphine salts. This material was distilled in vacuo to yield 1.6 g of title B compound, b.p. 110° C./ 0.05 cm.

$[\alpha]_D$= −54° $[\alpha]_{365}{}^{Hg}$= −168° C=11 mg/ml CHCl$_3$

TLC: silica gel; ethyl acetate/dichloromethane (1:1); $R_f$=0.2; vanillin spray and heat.

C.
[(4aR)-cis-exo]-Octahydro-5,8-epoxy-1H-benzopyran-3-ol

A solution of title B compound (1.6 g, 0.0087 mole) in 20% trifluoroacetic acid/water (16 ml) was stirred at room temperature under nitrogen for 2 hours. The solution was made basic with solid sodium bicarbonate. The aqueous mixture was then saturated with sodium chloride and extracted with chloroform (10×50 ml). The combined extracts wre concentrated in vacuo. The resultant oil contained significant amounts of partial hydrolysis products. This material was subjected to a second treatment with TFA/water as above and after a second workup as above yielded a solid product which was chromatographed on LP-1 silica gel (150 ml) eluting with ether/dichloromethane (1:9) and ether to yield 1.3 g of title C compound, m.p. 94°–96° C.

TLC: silica gel; ethyl acetate/dichloromethane (1:1); $R_f=0.1$; vanillin spray and heat.

$[\alpha]_D = -26.8°$ C=10 mg/ml MeOH

D.
[1S-(1α,2β(Z),3β,4α)]-7-[3-(Hydroxymethyl)-7-oxabicyclo-[2.2.1]hept-2-yl]-5-heptenoic acid and

E.
[1S-(1α,2β(Z),3β,4α)]-7-[3-(Hydroxymethyl)-7-oxabicyclo-[2.2.1]hept-2-yl]-5-heptenoic acid, methyl ester A slurry of 4-carboxybutyltriphenylphosphonium bromide (10.18 g, 0.023 mole) in anhydrous dimethylsulfoxide (20 ml) was treated with a solution of freshly prepared dimsyl ion at 15° C. until an orange coloration persisted. A second equivalent of dimsyl ion was added to form the desired ylide. The deep red mixture was stirred at room temperature for 30 minutes then treated with title compound (1.3 g, 0.0076 mole) dissolved in 10 ml of anhydrous dimethylsulfoxide. The reaction mixture was stirred at room temperature for 2 hours then quenched with a solution of glacial acetic acid (1.4 g, 0.023 mole) in ether (10 ml). The mixture was poured into brine (1000 ml), acidified to pH=2 with concentrated hydrochloric acid and extracted with ethyl acetate (6×50 ml). The combined extracts were concentrated in vacuo. The residue was dissolved in 5% sodium bicarbonate (150 ml) and extracted with benzene (2×100 ml) and ethyl acetate (2×100 ml). The aqueous layer was acidified to pH=2 with concentrated hydrochloric acid and extracted with ethyl acetate (5×50 ml). The combined ethyl acetate extracts were dried over magnesium sulfate and concentrated in vacuo. The residue was dissolved in ether (100 ml) and chilled overnight. The precipitated phosphine salts were removed by filtration. The filtrate was concentrated in vacuo to yield 2.1 g of product which contained title D compound contaminated with small amounts of phosphine salts. Title D compound was dissolved in 100 ml of ether, treated with excess ethereal diazomethane solution and stirred at room temperature for 1 hour. The reaction mixture was quenched with glacial acetic acid/ether solution, washed with 5% sodium bicarbonate, then concentrated in vacuo. The residue was chromatographed on LP-1 silica gel (400 ml) eluting with ether/hexane (1:1) and ether to yield 1.4 g of title E compound.

TLC of title D compound: silica gel; ether; $R_f=0.2$; vanillin spray and heat.

TLC of title E compound: silica gel; ether; $R_f=0.4$; vanillin spray and heat.

$[\alpha]_D$ of title E compound = $-12.3°$ C=27 mg/ml (MeOH).

EXAMPLE 3

[1S-[1α(1S),3aα,4α,7α,7aα]]Octahydro-1-[[2-oxo-7,7-dimethylbicyclo[2.2.1]-heptane]-carboxyl]-4,7-epoxyisobenzofuran Following the procedure of Example 1 except substituting dextro-menthol for levo-menthol and dextro-ketopinic acid for levo-ketopinic acid, the title compound is obtained.

EXAMPLE 4

[1R-(1α,2β(Z),3β,4α)]-7-[3-(Hydroxymethyl)-7-oxabicyclo[2.2.1]hept-2-yl]-5-heptenoic acid, methylester Following the procedure of Example 2 except substituting the Example 3 isomer for the Example 1B isomer, the title compound is obtained.

What is claimed is:

1. An optically active cis exo isomer having the structure

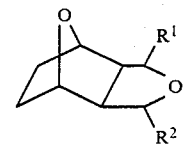

wherein one of $R^1$ and $R^2$ is

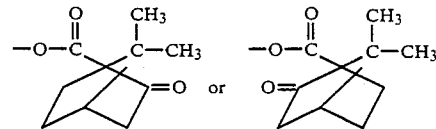

and the other is H.

2. The compound as defined in claim 1 wherein $R^1$ is

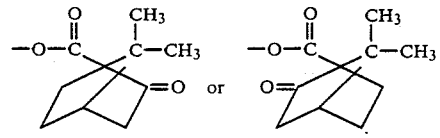

3. The compound as defined in claim 1 wherein $R^2$ is

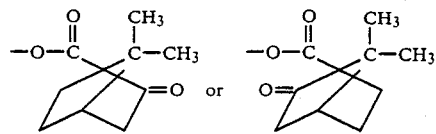

4. The compound as defined in claim 1 having the structure

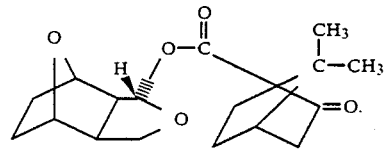

cis exo

5. The compound as defined in claim 1 having the structure

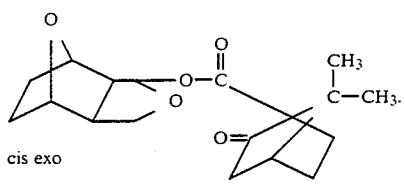

cis exo

6. The compound as defined in claim 1 having the structure

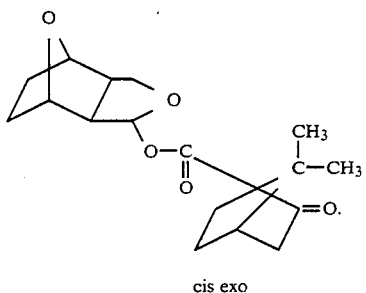

cis exo

7. The compound as defined in claim 1 having the structure

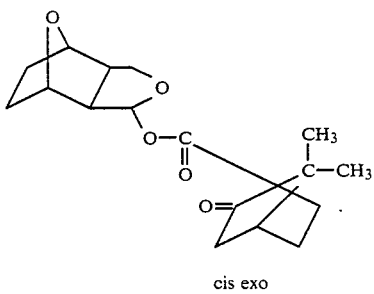

cis exo

8. A method for preparing an optically active ketopinate ester of the structure

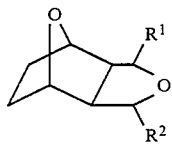

wherein one of $R^1$ and $R^2$ is

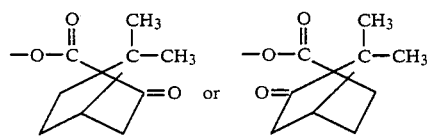

and the other is H which comprises esterifying a hemiacetal of the formula

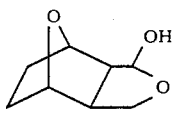

by reacting same with d or l-menthol to form a mixture of diastereomers, resolving the above mixture to recover 90% optically pure diastereomer of the structure

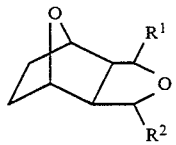

wherein $R^2$ is

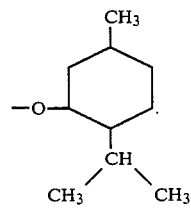

and $R^1$ is H, reacting the above hemiacetal with benzyl alcohol to form the optically active compound

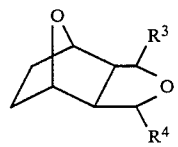

wherein $R^4$ is

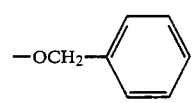

and $R^3$ is H, hydrogenating the benzyloxy compound to form a hemiacetal of the structure

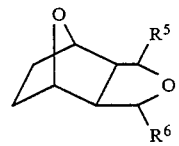

wherein $R^6$ is OH and $R^5$ is H, reacting the hemiacetal with l or d-ketopinic acid halide to form the optically active ketopinate ester.

* * * * *

UNITED STATES PATENT AND TRADEMARK OFFICE
CERTIFICATE OF CORRECTION

PATENT NO. : 4,500,723
DATED : February 19, 1985
INVENTOR(S) : Peter W. Sprague et al.

It is certified that error appears in the above—identified patent and that said Letters Patent is hereby corrected as shown below:

Column 8, lines 12, 13 and 16, "O" should read --Q--.

Signed and Sealed this

Twenty-fourth Day of September 1985

[SEAL]

Attest:

DONALD J. QUIGG

Attesting Officer

Commissioner of Patents and Trademarks—Designate